United States Patent [19]

Brandt et al.

[11] Patent Number: 5,489,663
[45] Date of Patent: Feb. 6, 1996

[54] PREPARATION OF POLYISOCYANATES CONTAINING ISOCYANURATE GROUPS AND USE THEREOF

[75] Inventors: Peter Brandt; Bernd Bruchmann, both of Ludwigshafen; Gerhard Laqua, Mannheim; Franz Merger, Frankenthal; Andreas Otterbach, Frankenthal; Konrad Stiefenhöfer, Ebertsheim; Tom Witzel, Ludwigshafn; Stefan Wolff, Limburgerhof; Rainer Becker, Bad Dürkheim, all of Germany

[73] Assignee: BASF Aktiengesellschaft, Germany

[21] Appl. No.: 356,084

[22] Filed: Dec. 15, 1994

[51] Int. Cl.$^6$ .......................... C08G 18/20; C08G 18/16
[52] U.S. Cl. ................ 528/52; 528/53; 528/54; 528/73; 544/193
[58] Field of Search ................ 528/73, 52, 53, 528/54; 544/193

[56] References Cited

U.S. PATENT DOCUMENTS

| | | | |
|---|---|---|---|
| 2,635,100 | 4/1953 | Werntz | 544/65 |
| 3,703,520 | 11/1972 | Carleton et al. | 544/351 |
| 3,980,594 | 9/1976 | Fabres et al. | 521/198 |
| 4,040,992 | 8/1977 | Bechara et al. | 544/180 |
| 4,454,317 | 6/1984 | Disteldorf et al. | 544/193 |
| 4,530,796 | 7/1985 | Mattner et al. | 560/345 |
| 4,731,427 | 3/1988 | Younes | 528/53 |
| 5,013,838 | 5/1991 | Schall | 544/193 |

FOREIGN PATENT DOCUMENTS 0512213  11/1992  European Pat. Off. .

OTHER PUBLICATIONS

EPO Search Report dated Mar. 19, 1995; Translation of EPO Search Report.

*Primary Examiner*—James J. Seidleck
*Assistant Examiner*—R. F. Johnson
*Attorney, Agent, or Firm*—Dennis V. Carmen

[57] ABSTRACT

Polyisocyanates containing isocyanurate groups are prepared by a partial trimerization of (cyclo)aliphatic diisocyanates in the presence of at least one trimerization catalyst selected from the group consisting of tetraalkylammonium alkyl carbonates of the formula (I)

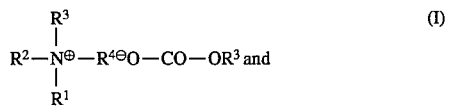

(quaternary ammonioalkyl) carbonates having a betaine structure of the formula (II)

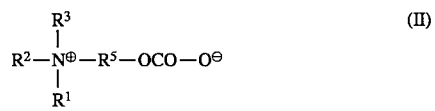

and the preferred use of the polyisocyanates containing isocyanurate groups which are obtainable in this way is as polyisocyanate component in polyurethane finishes.

22 Claims, No Drawings

PREPARATION OF POLYISOCYANATES CONTAINING ISOCYANURATE GROUPS AND USE THEREOF

The present invention relates to a novel process for preparing polyisocyanates containing isocyanurate groups by partial trimerization of (cyclo)aliphatic diisocyanates, preferably (cyclo)aliphatic diisocyanates obtainable by phosgene-free processes, in the presence of at least one trimerization catalyst selected from the group consisting of tetraalkylammonium alkyl carbonates and (quaternary ammonioalkyl) carbonates having a betaine structure and the preferred use of the polyisocyanates containing isocyanurate groups obtainable in this way as polyisocyanate component in polyurethane finishes.

Processes for the partial or complete trimerization of organic polyisocyanates to prepare polyisocyanates containing isocyanurate groups or cellular or compact polyurethanes containing isocyanurate groups are known and are described in numerous literature publications, such as the Kunststoff-Handbuch, Polyurethane, volume 7, 2nd edition 1983 (page 81) published by Dr. G. Oertel, Carl Hanser Verlag, Munich, Vienna, in Polyurethanes, Chemistry and Technology, Part I, 1962, by J. H. Saunders and K. C. Frisch, (page 94), Advances in Urethane Science and Technology, Vol. 3, (Technomic Publishing Co., Inc. 1974, page 141) and Plaste und Kautschuk 23, pages 162ff and 177ff (1976), and Patents. Suitable trimerization catalysts which may be mentioned are, for example, alkali metal oxides, alkali metal hydroxides and strong organic bases such as alkali metal alkoxides, alkali metal phenoxides, metal salts of carboxylic acids, for example cobalt naphthenate, sodium benzoate, sodium acetate and potassium formate, tertiary amines, for example triethylamine, N,N-dimethylbenzylamine, tri-ethylenediamine, tris-2,4,6-(dimethylaminomethyl)phenol and tris-1,3,5-(dimethylaminopropyl)-S-hexahydrotriazine, tertiary phosphines and tertiary ammonium compounds.

According to DE-A-38 06 276, trimerization catalysts which have proven useful are quaternary ammonium hydroxides, preferably N,N,N-trimethyl-N-benzylammonium hydroxide and N,N,N-tri-methyl-N-(2-hydroxypropyl)ammonium hydroxide. A disadvantage of these catalysts is that they are very sensitive to impurities and the diisocyanates used for the trimerization have to be freed of carbon dioxide down to a residual content of less than 20 ppm. EP-A-0 339 396 (U.S. Pat. No. 4,960,848) describes quaternary ammonium fluorides as trimerization catalyst and EP-A-0 379 914 (U.S. Pat. No. 5,013,838) specifies quaternary ammonium or phosphonium fluorides as catalysts, with the trimerization being carried out in the presence of carbon dioxide passed into the reaction mixture. A disadvantage of the trimerization catalysts specified is that, in the reaction of hexamethylenediisocyanate, also abbreviated to HDI, they give predominantly turbid products which are unusable in the surface finish application. Turbidity-free polyisocyanates containing isocyanurate groups are obtained, according to EP-A-0 010 589 (U.S. Pat. No. 4,324,879), using hydroxyalkyl-substituted quaternary ammonium hydroxides as catalyst. Disadvantages of this process are that the hydroxyalkylammonium hydroxides are very difficult to prepare in colorless form and have to be used in relatively large amounts, for example in amounts of up to 0.6% by weight. The polyisocyanates containing isocyanurate groups and freed of excess HDI can therefore be yellowish. For the trimerization and polymerization of polyisocyanates and for the polyaddition of polyisocyanates and polyols, U.S. Pat. No. 3,817,939 describes catalysts which are organic metal salts of the formula $(A)_n-R-CO-O^\ominus M^\oplus$, where A is hydroxyl or hydrogen, n is from 1 to 3, R is a polyfunctional, linear or branched, aliphatic or aromatic hydrocarbon radical and M is a cation of a strong base, eg. an alkali metal cation or a quaternary ammonium cation such as tetraalkylammonium. U.S. Pat. No. 3,703,520 specifies, as trimerization catalysts, adducts of ethylene carbonate and triethylenediamine in essentially equimolar ratios. In this process too, disadvantages are the relatively high amounts of catalyst, from 0.5 to 5% by weight based on the amount of polyisocyanate, which are required for the trimerization. DE-A-26 31 733 (U.S. Pat. No. 4,040,992) describes a process for preparing polyurethanes and polyisocyanurates from organic polyisocyanates and, if desired, polyols in the presence of quaternary hydroxyalkylammonium compounds of the formula

as catalyst. Disadvantages of these catalysts are their thermal lability, so that they can only be used in a narrow temperature range, and their low catalytic activity which can lead to discoloration of the final product.

Also known are the preparation of quaternary ammonium carbonates by reaction of tertiary amines and dialkyl carbonates in a preferred molar ratio of from 2:1 to 3:1 as described in U.S. Pat. No. 2,635,100 and betaine-type monoesters of carbonic acid of the formula

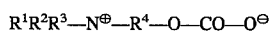

and also a process for their preparation described in EP-A-0 400 435. Not described in the specified patent publications is the use of the quaternary ammonium carbonates and betaine-type monoesters of carbonic acid for preparing polyisocyanates containing isocyanurate groups.

It is an object of the present invention to reproducibly prepare essentially colorless polyisocyanates containing isocyanurate groups, which can be used as polyisocyanate component for, preferably, polyurethane (PU) finish systems, by a very simple process in very good quality, preferably from (cyclo)aliphatic diisocyanates obtainable by phosgene-free processes.

We have found that this object is achieved by the use of tetraalkylammonium alkyl carbonates and/or (quaternary ammonioalkyl) carbonates having a betaine structure as trimerization catalyst.

The present invention accordingly provides a process for preparing polyisocyanates containing isocyanurate groups by partial trimerization of aliphatic and/or cycloaliphatic diisocyanates in the presence of at least one trimerization catalyst and deactivation of the trimerization catalyst after reaching the desired degree of trimerization, wherein the trimerization catalysts used are tetraalkylammonium alkyl carbonates of the formula (I)

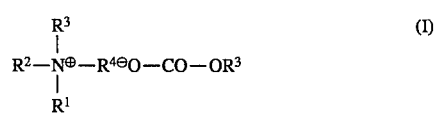

or (quaternary ammonioalkyl) carbonates having a betaine structure and the formula (II)

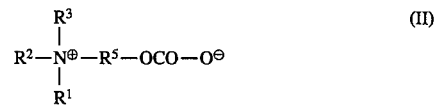

or mixtures of (I) and (II), where $R^1$, $R^2$ and $R^4$ are identical or different and are a $C_1$- to $C_{20}$-alkyl group, preferably a $C_1$- to $C_6$-alkyl group, a $C_5$- or $C_6$-cycloalkyl group, a $C_7$- to $C_{10}$-aralkyl group, preferably a $C_7$-aralkyl group, or a phenyl group, or where $R^1$ and $R^2$ together form a 5-membered or 6-membered cycloalkyl group or, together with a nitrogen atom, form a 5-membered or 6-membered ring which can contain an additional nitrogen or oxygen atom as a bridge member, or where $R^1$, $R^2$ and $R^4$ together form a multi-membered, preferably six-membered, multi-ring system, preferably a two-ring system, which can contain one or more additional nitrogen atoms, oxygen atoms or nitrogen and oxygen atoms as bridge members, $R^3$ is a $C_1$- to $C_4$-alkyl group, preferably a methyl group, $R^5$ is a $C_2$- to $C_{20}$-alkylene group, preferably a $C_2$- to $C_{12}$-alkylene group, a $C_5$- or $C_6$-cycloalkylene group, a $C_7$- to $C_{10}$-aralkylene group, preferably a benzylene group or a phenylene group or $R^5$ and $R^1$ together are an alkylene group and together with a nitrogen atom as a bridge member form a 5-membered to 7-membered, preferably 6-membered, heterocyclic ring.

The tetraalkylammonium alkyl carbonates and (quaternary ammonioalkyl) carbonates having a betaine structure which can be used according to the invention as trimerization catalysts are thermally stable at temperatures above 100° C. and are thus catalytically active over a temperature range from about 20° to 180° C., while the quaternary hydroxyalkylammonium carboxylates described in DE-A-26 31 733 are, because of their thermal lability, generally only usable at temperatures of from 60° to 80° C. Higher trimerization temperatures, for example above 95° C., are advantageously used for the trimerization of sterically hindered diisocyanates, such as isophorone diisocyanate or 2-butyl-2-ethylpentane-1,5-diisocyanate, since this can achieve higher space-time yields. The reaction rate of the trimerization reaction can, using the tetraalkylammonium alkyl carbonates of the invention, be increased by a factor of from 2 to 8, and using the (quaternary ammonioalkyl) carbonates having a betaine structure be increased by a factor of from 15 to 20, or the amount of the catalysts of the invention used can be considerably decreased in comparison with, for example, N-(2-hydroxypropyl-N,N,N-trimethylammonium mono-2-ethylhexanoate.

The novel trimerization catalysts of the invention can be used for trimerizing (cyclo)aliphatic diisocyanates prepared by any processes. However, they have proven particularly useful and are therefore preferably used for the trimerization of (cyclo)aliphatic diisocyanates prepared by phosgene-free processes, since in this way it is not only possible to considerably increase the reaction rate of the trimerization reaction, but polyisocyanates containing isocyanurate groups which have extremely low Hazen color numbers, eg. preferably less than 35, are also obtained.

As already mentioned, the trimerization catalysts which can be used according to the invention can be prepared by known processes. Tetraalkylammonium alkyl carbonates of the formula (I), preferably trialkylmethylammoniummethyl carbonate, can be prepared by reacting, for example, dialkyl carbonates, preferably dimethyl carbonate, with tertiary amines in the absence or presence of solvents, eg. chlorobenzene, at temperatures of advantageously from 100° to 180° C. Examples of suitable tertiary amines which may be mentioned are: N,N'-dimethylpiperazine, N-methoxyphenylpiperazine, N-methylpiperidine, N-ethylpiperidine, quinuclidine, trialkylamines such as trimethylamine, triethylamine and tripropylamine, and preferably 1,4-dimethylpiperazine, N,N-dimethylbenzylamine and triethylenediamine.

The tetraalkylammonium alkyl carbonates preferably used as trimerization catalysts, which like other suitable tetraalkylammonium alkyl carbonates can be used individually or in the form of mixtures, have the formulae (III) to (V)

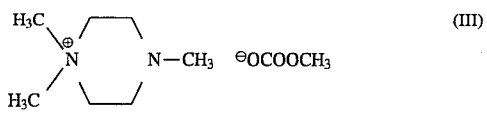
(III)

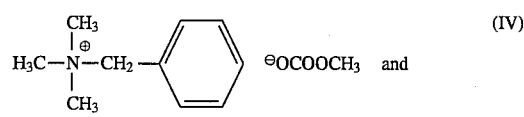
(IV)

(V)

The preparation of the (quaternary ammonioalkyl) carbonates having a betaine structure and the formula (II) can be carried out, for example, by reaction of dialkyl carbonates, preferably dimethyl carbonate, with hydroxyl-containing tertiary amines at temperatures of from 25° to 200° C. in accordance with EP-A-400 435.

Examples of suitable hydroxyl-containing tertiary amines which may be mentioned are: N,N-dialkylaminoalkanols such as N,N-dimethylaminoethanol, N,N-dimethylaminobutanol, N,N-dimethylaminooctanol, N,N-diethylaminoethanol, N,N-diethylaminopropanol, N,N-diethylaminobutanol, N,N-diethylaminopentanol, N,N-diisopropylaminoethanol, N-butyl-N-methylaminopropanol, N-cyclohexyl-N-methylaminoethanol, N-benzyl-N-propylaminoethanol, N-hydroxyethylpyrrolidine, N-hydroxyethylpiperidine, N-hydroxylethylmorpholine, N-hydroxypropylpyrrolidine, N-hydroxypropylpiperidine, N-hydroxypropylmorpholine, 3-hydroxyquinuclidine, N,N-dimethylaminoneopentanol, 1-hydroxymethyl-1-dimethylaminomethylcyclohexane, N,N-diethylaminoneopentanol, N,N-dibutylaminoneopentanol, pyrrolidinoneopentanol, piperidinoneopentanol, 3-hydroxymethyl-3-dimethylaminomethylheptane, 3-hydroxymethyl- 3-diethylaminomethylheptane, 3-hydroxymethyl-3-(N-methyl-N-hexylamino)heptane, (N-methoxyethyl-N-methylamino)ethanol, (N-butoxyethyl-N-ethylamino)ethanol, (N-phenoxyethyl-N-methylamino)propanol, N-methyl-3-pyrrolidinol, and preferably N,N-dimethylaminopropanol, N,N-dimethylaminohexanol and N-methyl-4-piperidinol.

The (quaternary ammonioalkyl) carbonates having a betaine structure and preferably used as trimerization catalysts, which like other suitable (quaternary ammonioalkyl) carbonates having a betaine structure can be used individually or in the form of mixtures, have the formulae (VI) to (VIII)

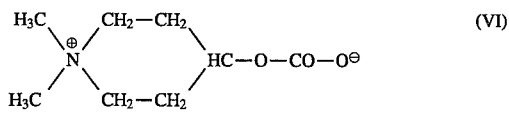
(VI)

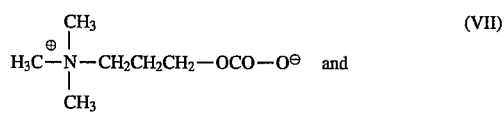
(VII)

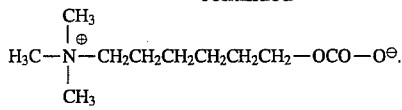

(VIII)

As trimerization catalysts, it is also possible to use mixtures of tetraalkylammonium alkyl carbonates (I) and tetraalkylammonium carbonates having a betaine structure (II), with these being able to be mixed in a wide range of ratios, for example in ratios of from 90:10 to 10:90 and preferably from 60:40 to 40:60.

To prepare the polyisocyanates containing isocyanurate groups, the trimerization catalysts of the invention are, depending on their catalytic activity, advantageously used in very small effective amounts which can be experimentally determined in a simple manner.

In the process of the invention, the tetraalkylammonium alkyl carbonates (I) are generally used in an amount of from 0.002 to 0.05% by weight, preferably from 0.005 to 0.02% by weight, and the (quaternary ammonioalkyl) carbonates having a betaine structure (II) are used in an amount of from 0.001 to 0.03% by weight, preferably from 0.002 to 0.01% by weight, in each case based on the weight of the (cyclo)aliphatic diisocyanates.

The process of the invention is advantageously carried out at a temperature in the range from 30° to 150° C. At temperatures below 30° C., there can be gel formation which is attributable to a linear polymerization of the (cyclo)aliphatic diisocyanates to give nylon-1 structures. At temperatures above 150° C., discoloration of the polyisocyanates containing isocyanurate groups can occur, for example at relatively long reaction times.

When using tetraalkylammonium alkyl carbonates (I), reaction temperatures above 80° C., in particular from 85° to 120° C., are preferably used, while when using (quaternary ammonioalkyl) carbonates having a betaine structure (II), reaction temperatures below 80° C. are preferred, with essentially colorless trimerization products being obtained, in particular at reaction temperatures of from 60° to 40° C.

After reaching the desired degree of trimerization or NCO content in the isocyanurate/(cyclo)aliphatic diisocyanate reaction mixture, which is advantageously in the range from 45 to 25% by weight of NCO groups, preferably from 43 to 38% by weight of NCO groups, and for which purpose reaction times of from 0.05 to 4 hours, preferably from 1 to 2 hours, are usually required, the trimerization reaction is stopped by deactivation of the trimerization catalysts. Suitable deactivators are, for example, inorganic acids such as hydrochloric acid, phosphorous acid or phosphoric acid, carbonic acid halides such as acetyl chloride or benzoyl chloride, sulfonic acids or esters such as methane-sulfonic acid, p-toluenesulfonic acid, methyl or ethyl p-toluenesulfonate, m-chloroperbenzoic acid and preferably dialkyl phosphates such as di-2-ethylhexyl phosphate and in particular dibutyl phosphate. The deactivators can be used in equivalent, excess or deficient amounts based on the trimerization catalysts, with preference being given to the smallest effective amount, which can be experimentally determined, if only for economic reasons.

The process of the invention is preferably carried out in the absence of solvent. However, if the (cyclo)aliphatic diisocyanates are partially trimerized in the presence of solvents or diluents, use may be made both of inert nonpolar and of inert polar solvents or diluents such as toluene, xylene, cyclic ethers, carbonic esters and ketones or mixtures thereof.

The polyisocyanates containing isocyanurate groups which are prepared by the process of the invention can be freed of any solvent or diluent present and/or preferably of excess, unreacted (cyclo)aliphatic diisocyanates in a manner known per se, for example by thin-film distillation or extraction, so that the polyisocyanates containing isocyanurate groups are obtainable with a content of monomeric diisocyanates of, for example, below 1.0% by weight, preferably below 0.5% by weight.

The excess monomeric diisocyanates are advantageously removed when the process products are used for the production of polyurethane finishes. Without removal of the excess monomeric diisocyanates, the polyisocyanates containing isocyanurate groups are useful, for example, for producing PU foam materials, cellular or compact elastomers, sealing compositions and adhesives. The monomer-free and monomer-containing polyisocyanates containing isocyanurate groups can also be modified in a manner known per se by introducing, for example, urethane, allophanate, urea, biuret and/or carbodiimide groups and/or the isocyanate groups can be blocked using suitable blocking agents such as ε-caprolactam, dimethyl malonate, acetoacetic esters or aromatic hydroxyl groups.

The process of the invention can be used to trimerize any organic diisocyanates having aliphatic, cycloaliphatic or aliphatic and cycloaliphatic isocyanate groups or mixtures thereof.

Suitable aliphatic diisocyanates advantageously have from 3 to 16 carbon atoms, preferably from 4 to 12 carbon atoms, in the linear or branched alkylene radical and suitable cycloaliphatic diisocyanates advantageously have from 4 to 18 carbon atoms, preferably from 6 to 15 carbon atoms, in the cycloalkylene radical. Examples which may be mentioned are: 1,4-diisocyanatobutane, 2-ethyl-1,4-diisocyanatobutane, 1,5-diisocyanatopentane, 2-methyl-1,5-diisocyanatopentane, 2,2-dimethyl-1,5-diisocyanatopentane, 2-propyl-2-ethyl-1,5-diisocyanatopentane, 2-butyl-2-ethyl-1,5-diisocyanatopentane, 2-alkoxymethylene- 1,5-diisocyanatopentane, 3-methyl-, 3-ethyl-1,5 -diisocyanatopentane, 1,6-hexamethylenediisocyanate, 2,4,4- or 2,2,4-trimethyl-1,6-hexamethylenediisocyanate, 1,7-diisocyanatoheptane, 1,8-diisocyanatooctane, 1,10-diisocyanatodecane, 1,12-diisocyanatododecane, 4,4'-diisocyanatodicyclohexylmethane, 2,4'-diisocyanatodicyclohexylmethane and also mixtures of the diisocyanatodicyclohexylmethane isomers, 1,3-diisocyanatocyclohexane and also mixtures of isomers of diisocyanatocyclohexanes and 1-isocyanato-3-isocyanatomethyl-3,5,5-trimethylcyclohexane. (Cyclo)aliphatic diisocyanates preferably used are 1,6-hexamethylenediisocyanate, isomeric aliphatic diisocyanates having 6 carbon atoms in the alkylene radical and also mixtures thereof, 2-butyl-2-ethyl-1,5-diisocyanatopentane and 1-isocyanato-3 -isocyanatomethyl-3,5,5-trimethylcyclohexane.

The (cyclo)aliphatic diisocyanates which can be used according to the invention can be prepared by any processes, for example by phosgenation of the corresponding diamines and thermal cleavage of the dicarbamic acid chlorides formed as intermediates. (Cyclo)aliphatic diisocyanates prepared by phosgene-free processes do not contain chlorine compounds as byproducts and therefore have a fundamentally different byproduct spectrum. It has surprisingly been found that, in the trimerization of (cyclo)aliphatic diisocyanates prepared by phosgene-free processes, the trimerization catalysts which can be used according to the invention have a significantly higher catalytic activity and give polyisocyanates containing isocyanurate groups with an appreciably lower color number than in the analogous reaction of (cyclo)aliphatic diisocyanates prepared by phosgenation. It has therefore proven to be advantageous in the process of the invention to use (cyclo)aliphatic diisocyanates obtainable by, preferably, a phosgene-free process and, in particular, by thermal cleavage of (cyclo)aliphatic dicarbamic esters, with particular preference being given to using diisocyanates obtainable by thermal cleavage of (cyclo)aliphatic dicarbamic esters and selected from the group consisting of 1,6-hexamethylenediisocyanate, 2-butyl-2-ethylpentamethylene-1,5-diisocyanate and 1-isocyanato-3-isocyanatomethyl-3,5,5-trimethylcyclohexane. Polyisocyanates containing isocyanurate groups prepared by these process variants are very useful for preparing polyurethane coatings, eg. textile and leather coatings, for polyurethane dispersions and adhesives and can be used, in particular, as polyisocyanate component in two-component polyurethane systems for high-performance, weather-resistant polyurethane finishes and high-solid finishes.

EXAMPLES

Catalyst Preparation

Preparation of tetraalkylammonium alkyl carbonates of the formula I

1. Preparation of 1,1-dimethyl-1-azonia-4-methyl-4-azacyclo[2.2]hexane monomethyl carbonate of the formula (III), hereinafter abbreviated as cat. 1

In a reaction vessel fitted with stirrer, reflux condenser and gas inlet and outlet, a mixture of 57.1 parts by weight (0.5 mol) of N,N'-dimethylpiperazine and 90.1 parts by weight (1 mol) of dimethyl carbonate was heated to 95° C. while stirring in an inert gas atmosphere (nitrogen) and reacted at this temperature for 8 hours. The excess dimethyl carbonate was then distilled off and the distillation residue obtained was taken up in 2500 parts by weight of methyl ethyl ketone. The 1,1-dimethyl-1-azonia-4-methyl-4-azacyclo[2.2]hexane monomethyl carbonate crystallized from the methyl ethyl ketone was filtered off with suction under an inert gas atmosphere and dried.

Elemental analysis ($C_9H_{20}N_2O_3$)

Calculated [% by wt.]: C 52.9; H 9.9; N 13.7; O 23.5

Found [% by wt.]: C 52.7; H 9.1; N 14.2; O 24.3

Decomposition range: 220° to 240'C.

2. Preparation of N,N,N-trimethylbenzylammonium-monomethyl carbonate of the formula (IV), hereinafter abbreviated as cat. 2

The preparation was carried out in a similar way to that of cat. 1, but using 67.6 parts by weight (0.5 mol) of N,N-dimethylbenzylamine in place of N,N'-dimethylpiperazine.

Elemental analysis ($C_{10}H_{19}NO_3$)

Calculated [% by wt.]: C 63.9;H 8.5;N 6.2;O 21.3

Found [% by wt.]: C 63.7;H 8.6;N 6.0;O 21.6

Decomposition range: 210° to 230° C.

3. Preparation of 1-methyl-1-azonia-4-azabicyclo[2.2.2]octane monomethyl carbonate of the formula (V), hereinafter abbreviated as cat. 3

The preparation was carried out in a similar way to that of cat. 1, but using 56.1 parts by weight (0.5 mol) of diazabicyclo[2.2.2]octane in place of N,N'-dimethylpiperazine.

Elemental analysis ($C_9H_{18}N_2O_3$)

Calculated [% by wt.]: C 51.3; H 8.1; N 15.0; O 25.6

Found [% by wt.]: C 51.3; H 8.6; N 14.3; O 25.3

Decomposition range: 220° to 240° C.

Preparation of (quaternary ammonioalkyl) carbonates having a betaine structure and the formula (II)

4. Preparation of 4-(N,N-dimethylpiperidino) carbonate of the formula (VI), hereinafter abbreviated as cat. 4

In a reaction vessel fitted with stirrer, reflux condenser and gas inlet and outlet, a mixture of 73.6 parts by weight (0.5 mol) of N-methyl-4-piperidinol and 90.1 parts by weight (1.0 mol) of dimethyl carbonate was heated to 95° C. while stirring in an inert gas atmosphere (nitrogen) and reacted at this temperature for 8 hours. The excess dimethyl carbonate was then distilled off and the distillation residue obtained was taken up in 2000 parts by weight of methyl ethyl ketone. The 4-(N,N-dimethylpiperidino) carbonate crystallized from the methyl ethyl ketone was filtered off with suction under an inert gas atmosphere and dried.

Elemental analysis ($C_8H_{15}NO_3$)

Calculated [% by wt.]: C 55.5;H 8.7;N 8.1;O 27.7

Found [% by wt.]: C 55.3;H 8.9;N 8.3;O 27.5

Decomposition range: 240° to 260° C.

5. Preparation of N,N,N-trimethylammoniopropyl carbonate of the formula (VII), hereinafter abbreviated as cat. 5

The preparation was carried out in a similar way to that of cat. 4, but using 51.5 parts by weight (0.5 mol) of N,N-dimethylaminopropanol and 90.1 parts by weight (1 mol) of dimethyl carbonate as starting materials.

Elemental analysis ($C_7H_{15}NO_3$)

Calculated [% by wt.]: C 52.2; H 9.4; N 8.7; O 29.8

Found [% by wt.]: C 51.6; H 9.4; N 8.9; O 30.7

Decomposition range: 200° to 220° C.

6. Preparation of N,N,N-trimethylammoniohexyl carbonate of the formula (VIII), hereinafter abbreviated as cat. 6

The preparation was carried out in a similar way to that of cat. 4, but using 72.6 parts by weight (0.5 mol) of N,N-dimethylaminohexan-1-ol and 90.1 parts by weight (1 mol) of dimethyl carbonate as starting materials.

Elemental analysis ($C_{10}H_{21}NO_3$)

Calculated [% by wt.]: C 59.1; H 10.3; N 6.9; O 23.7

Found [% by wt.]: C 58.5; H 10.3; N 7.1; O 24.2

Decomposition range: 240° to 260° C.

Preparation of the polyisocyanates containing isocyanurate groups

Examples 1 to 19 and Comparative Examples I to III

The (cyclo)aliphatic diisocyanates were heated to a reaction temperature in the range from 30° to 110° C. while stirring in an inert gas atmosphere, eg. nitrogen or argon, a catalyst solution was added and the diisocyanates were trimerized for a period of from 60 to 120 minutes. To stop the trimerization reaction, the catalyst was deactivated by addition of dibutyl phosphate.

The comparative catalyst used (in the Comparative Examples) was N-(2-hydroxypropyl)-N,N,N-trimethylammonium 2-ethylhexanoate, hereinafter abbreviated as cat. 0.

The Table below summarizes the (cyclo)aliphatic diisocyanates used, the catalyst type, amount and solution, the reaction temperature and time and the isocyanate content and the color number of the polyisocyanates containing isocyanurate groups prepared.

In the Table:

HDI: is 1,6-hexamethylenediisocyanate prepared by thermal cleavage of hexamethylenedibutylurethane IPDI: is 1-isocyanato-3-isocyanatomethyl-3,5,5-trimethylcyclohexane BEPDI: is 2-butyl-2-ethylpentamethylene-1,5-diisocyanate

TABLE

| | Diisocyanate | Catalyst Type | Catalyst Amount [ppm] | Solution [% strength by wt.] in solvent | | Reaction conditions Temperature [°C.] | Time [min] | Polyisocyanates containing isocyanurate groups NCO content [% by wt.) | Hazen color number |
|---|---|---|---|---|---|---|---|---|---|
| Comparative Example | | | | | | | | | |
| I | HDI | Cat. 0 | 400 | 25 | 1,3-butanediol | 80 | 60 | 41.4 | 31 |
| II | HDI | Cat. 0 | 400 | 25 | isopropanol | 80 | 60 | 43.3 | 109 |
| III | HDI | Cat. 0 | 350 | 25 | benzyl alcohol | 80 | 60 | 40.2 | 56 |
| Example | | | | | | | | | |
| 1 | HDI | Cat. 1 | 200 | 25 | 1,3-butanediol | 80 | 60 | 40.1 | 28 |
| 2 | HDI | Cat. 2 | 100 | 25 | 1,3-butanediol | 80 | 60 | 41.2 | 20 |
| 3 | HDI | Cat. 2 | 50 | 25 | isopropanol | 80 | 60 | 43.8 | 33 |
| 4 | HDI | Cat. 3 | 50 | 70 | n-butanol | 90 | 60 | 42.9 | 34 |
| 5 | HDI | Cat. 4 | 25 | 25 | isopropanol | 80 | 60 | 42.1 | <10 |
| 6 | HDI | Cat. 4 | 25 | 25 | benzyl alcohol | 80 | 60 | 31.5 | 10–14 |
| 7 | HDI | Cat. 5 | 35 | 25 | benzyl alcohol | 80 | 60 | 38.4 | 22 |
| 8 | HDI | Cat. 6 | 210 | 25 | benzyl alcohol | 80 | 60 | 42.6 | 38 |
| 9 | HDI | Cat. 4 | 150 | 5 | benzyl alcohol | 60 | 60 | 40.1 | 0 |
| 10 | HDI | Cat. 4 | 125 | 5 | isopropanol | 60 | 60 | 42.3 | 0 |
| 11 | HDI | Cat. 5 | 138 | 5 | benzyl alcohol | 60 | 60 | 43.3 | 14 |
| 12 | HDI | Cat. 6 | 250 | 10 | benzyl alcohol | 60 | 90 | 41.7 | 11 |
| 13 | HDI | Cat. 4 | 105 | 25 | benzyl alcohol | 40 | 90 | 42.3 | 0 |
| 14 | HDI | Cat. 5 | 105 | 25 | benzyl alcohol | 40 | 90 | 42.8 | 0 |
| 15 | HDI | Cat. 4 | 100 | 25 | benzyl alcohol | 30 | 120 | 43.9 | 0 |
| 16 | IPDI | Cat. 2 | 750 | 25 | 1,3-butanediol | 95 | 115 | 29.3 | 115 |
| 17 | BEPDI | Cat. 2 | 750 | 25 | isopropanol | 100–110 | 60 | 29.3 | 149 |
| 18 | IPDI | Cat. 4 | 750 | 25 | methanol | 95 | 60 | 33.9 | 250 |
| 19 | BEPDI | Cat. 4 | 750 | 25 | methanol | 100 | 60 | 27.6 | 136 |

We claim:

1. A process for preparing polyisocyanates containing isocyanurate groups by partial trimerization of aliphatic and/or cycloaliphatic diisocyanates in the presence of at least one trimerization catalyst and deactivation of the trimerization catalyst after reaching the desired degree of trimerization, wherein the trimerization catalysts used comprise tetraalkylammonium alkyl carbonates of the formula (I)

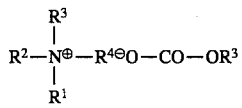

or mixtures with (quaternary ammonioalkyl) carbonates having a betaine structure and the formula (II)

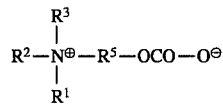

where $R^1$, $R^2$ and $R^4$ are identical or different and are a $C_1$- to $C_{20}$-alkyl group, a $C_5$- to $C_6$-cycloalkyl group, a $C_7$- to $C_{10}$-aralkyl group or a phenyl group or where $R^1$ and $R^2$ together form a 5-membered or 6-membered cycloalkyl group or, together with a nitrogen atom, form a 5-membered or 6-membered ring which can contain an additional nitrogen or oxygen atom as a bridge member, or where $R^1$, $R^2$ and $R^4$ together form a multi-membered multi-ring system which can contain one or more additional nitrogen atoms and/or oxygen atoms as bridge members, $R^3$ is a $C_1$- to $C_4$-alkyl group, $R^5$ is a $C_2$- to $C_{20}$-alkylene group, a $C_5$- to $C_6$-cycloalkylene group, a $C_7$- to $C_{10}$-aralkylene group or a phenylene group or $R^5$ and $R^1$ together are an alkylene group and together with a nitrogen atom as bridge member form a 5-membered to 7-membered heterocyclic ring.

2. A process as claimed in claim 1, wherein the trimerization catalysts comprise tetraalkylammonium alkyl carbonates of the formulae

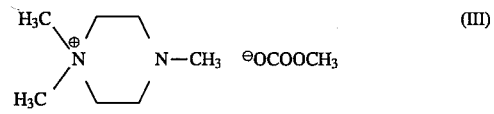

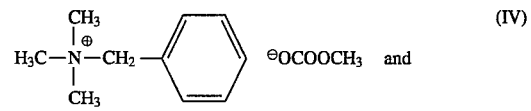

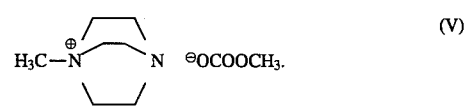

3. A process as claimed in claim 1, wherein the trimerization catalysts of formula II comprise (quaternary ammonioalkyl) carbonates having a betaine structure and the formulae

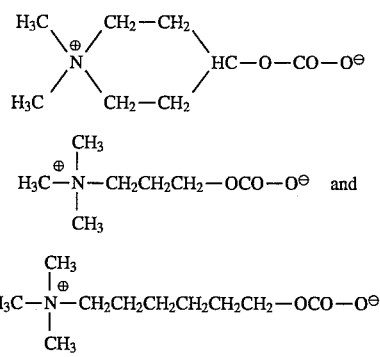

$$H_3C-\overset{\underset{|}{CH_3}}{\overset{\oplus}{N}}-CH_2CH_2CH_2-OCO-O^{\ominus} \text{ and} \quad (VII)$$
$$\phantom{H_3C-N-}\underset{CH_3}{|}$$

$$H_3C-\overset{\underset{|}{CH_3}}{\overset{|\oplus}{N}}-CH_2CH_2CH_2CH_2CH_2CH_2-OCO-O^{\ominus}. \quad (VIII)$$
$$\phantom{H_3C-N-}\underset{CH_3}{|}$$

4. A process as claimed in claim 1, wherein the partial trimerization is carried out at from 30° to 150° C.

5. A process as claimed in claim 1, wherein the tetraalkylammonium alkyl carbonates (I) or mixtures with (quaternary ammonioalkyl) carbonates having a betaine structure (II) are deactivated by addition of dibutyl phosphate.

6. A process as claimed in claim 1, wherein, after reaching the desired degree of trimerization and deactivating the trimerization catalyst, unreacted monomeric (cyclo)aliphatic diisocyanates are removed.

7. A process as claimed in claim 1, wherein the partial trimerization is carried out using (cyclo)aliphatic diisocyanates prepared by a phosgene-free process.

8. A process as claimed in claim 1, wherein the partial trimerization is carried out using (cyclo)aliphatic diisocyanates obtainable by thermal cleavage of (cyclo)aliphatic dicarbamic esters.

9. A process as claimed in claim 1, wherein the partial trimerization is carried out using (cyclo)aliphatic diisocyanates obtainable by thermal cleavage of (cyclo)aliphatic dicarbamic esters and selected from the group consisting of 1,6-hexamethylenediisocyanate, 2-butyl-2-ethylpentamethylene-1,5-diisocyanate and 1-isocyanato-3-isocyanatomethyl-3,5,5-trimethylcyclohexane.

10. A process as claimed in claim 1, comprising applying the polyisocyanate containing isocyanurate groups as a polyisocyanate component in a polyurethane finish.

11. A process as claimed in claim 1, comprising applying the polyisocyanate containing isocyanurate groups prepared from (cyclo)aliphatic diisocyanates in a phosgene free process as a polyisocyanate component in a polyurethane finish.

12. A process as claimed in claim 1, wherein said prepared polyisocyanates have a Hazen color number of less than 35.

13. A process for preparing polyisocyanates containing isocyanurate groups by partial trimerization of aliphatic and/or cycloaliphatic diisocyanates in the present of at least one trimerization catalyst and deactivation of the trimerization catalyst after reaching the desired degree of trimerization, wherein the trimerization catalysts used comprise reacting a dialkyl carbonate with an hydroxyl-containing tertiary amine to obtain (quaternary ammonioalkyl)carbonates having a betaine structure of the formula (II)

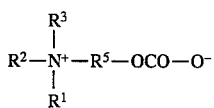

where $R^1$ and $R^2$ are identical or different and are a $C_1$- to $C_{20}$-alkyl group, a $C_5$- to $C_6$-cycloalkyl group, a $C_7$- to $C_{10}$-aralkyl group or a phenyl group or where $R^1$ and $R^2$ together form a 5-membered or 6-membered cycloalkyl group, or together with a nitrogen atom, form a 5-membered or 6-membered ring which can contain an additional nitrogen or oxygen atom as a bridge member, or where $R^1$, $R^2$ and $R^4$ together form a multi-membered multi-ring system which can contain one or more additional nitrogen atoms and/or oxygen atoms as bridge members, $R^3$ is a $C_1$- to $C_4$-alkyl group, $R^5$ is a $C_2$- to $C_{20}$-alkylene group, a $C_5$- to $C_6$-cycloalkylene group, a $C_7$- to $C_{10}$-aralkylene group or a phenylene group or $R^5$ and $R^1$ together are an alkylene group and together with a nitrogen atom as bridge member form a 5-membered to 7-membered heterocyclic ring.

14. A process as claimed in claim 13, wherein the trimerization catalysts are selected from among (quaternary ammonioalkyl) carbonates having a betaine structure and the formulae

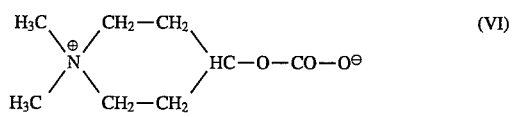

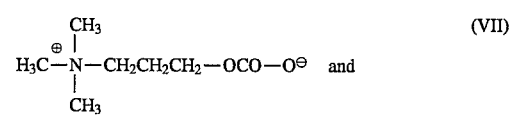

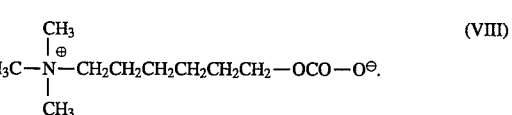

15. A process as claimed in claim 13, wherein the partial trimerization is carried out at from 30° to 150° C.

16. A process as claimed in claim 13, wherein the (quaternary ammonioalkyl) carbonates having a betaine structure (II) are deactivated by addition of dibutyl phosphate.

17. A process as claimed in claim 13, wherein, after reaching the desired degree of trimerization and deactivating the trimerization catalyst, the unreacted monomeric (cyclo)aliphatic diisocyanates are removed.

18. A process as claimed in claim 13, wherein the partial trimerization is carried out using (cyclo)aliphatic diisocyanates prepared by a phosgene-free process.

19. A process as claimed in claim 13, wherein the partial trimerization is carried out using (cyclo)aliphatic diisocyanates obtainable by thermal cleavage of (cyclo)aliphatic dicarbamic esters.

20. A process as claimed in claim 13, wherein the partial trimerization is carried out using (cyclo)aliphatic diisocyanates obtainable by thermal cleavage of (cyclo)aliphatic dicarbamic esters and selected from the group consisting of 1,6-hexamethylenediisocyanate, 2-butyl-2-ethylpentamethylene- 1,5-diisocyanate and 1-isocyanato-3-isocyanatomethyl-3,5,5 -trimethyl-cyclohexane.

21. A process as claimed in claim 13, comprising applying the polyisocyanate containing isocyanurate groups as a polyisocyanate component in a polyurethane finish.

22. A process as claimed in claim 13, comprising applying the polyisocyanate containing isocyanurate groups prepared from (cyclo)aliphatic diisocyanates in a phosgene-free process as a polyisocyanate component in a polyurethane finish.

* * * * *